US00PP21284P3

(12) United States Plant Patent
Meilland

(10) Patent No.: US PP21,284 P3
(45) Date of Patent: Sep. 14, 2010

(54) HYBRID TEA ROSE PLANT NAMED 'MEIBIDULL'

(50) Latin Name: *Rosa hybrida*
Varietal Denomination: Meibidull

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 206 days.

(21) Appl. No.: 12/232,812

(22) Filed: Sep. 24, 2008

(65) Prior Publication Data

US 2010/0077517 P1 Mar. 25, 2010

(51) Int. Cl.
*A01H 5/00* (2006.01)

(52) U.S. Cl. ..... Plt./137

(58) Field of Classification Search ..... Plt./137
See application file for complete search history.

(56) References Cited

U.S. PATENT DOCUMENTS

PP13,438 P3 * 12/2002 Yanagida ..... Plt./137

* cited by examiner

*Primary Examiner*—Wendy C. Haas
(74) *Attorney, Agent, or Firm*—Buchanan Ingersoll & Rooney PC

(57) ABSTRACT

A new and distinct variety of Hybrid Tea rose plant is provided that forms on a recurrent basis attractive fragrant double blossoms having a soft apricot-pink coloration. The buds are pointed and ovoid-shaped. The vegetation is vigorous and upright and attractive medium green foliage is formed. The disease resistance is above average for the class. The plant is particularly well suited for providing attractive ornamentation in the landscape.

1 Drawing Sheet

Figure 1:
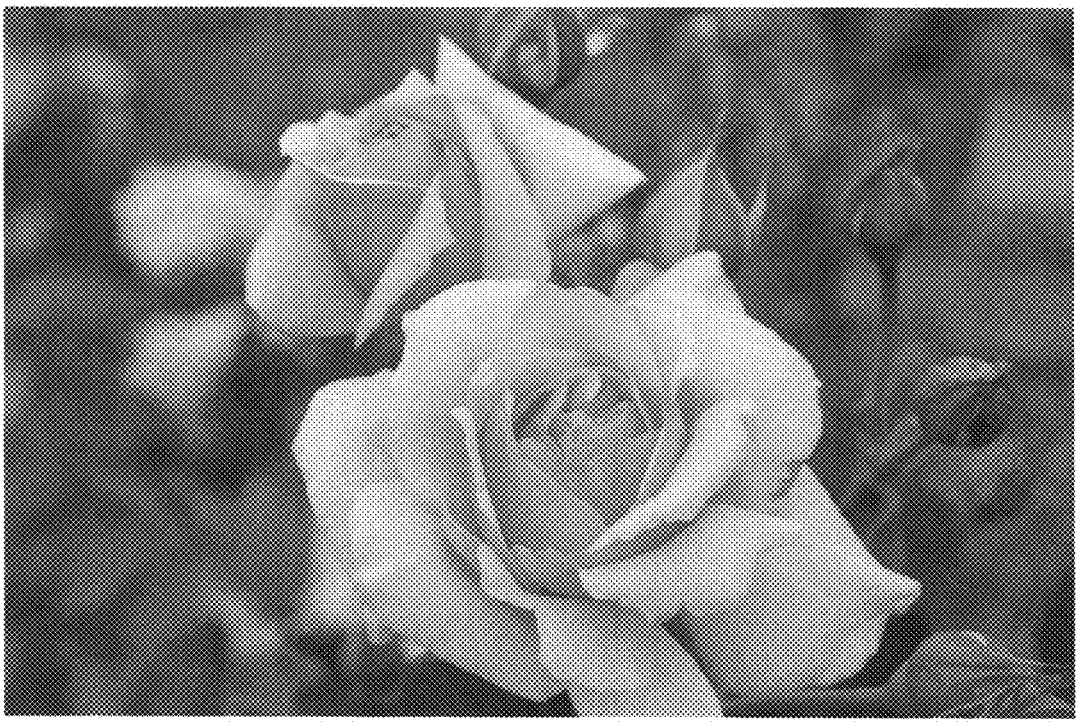

Botanical/commercial classification: *Rosa hybrida*/Hybrid Tea Rose Plant.

Varietal denomination: cv. Meibidull.

SUMMARY OF THE INVENTION

The new variety of *Rosa hybrida* Hybrid Tea rose plant was created in France by artificial pollination wherein two parents were crossed which previously had been studied in the hope that they would contribute the desired characteristics. The female parent (i.e., the seed parent) was the product of the cross of the 'Just Joey' variety (non-patented in the United States) and the 'Jactou' variety (U.S. Plant Pat. No. 8,706). The male parent (i.e., the pollen parent) was the product of the cross of the 'Meirouve' variety (non-patented in the United States) and the 'Meizole' variety (U.S. Plant Pat. application Publication No. 20030093845 filed Aug. 11, 2006, now abandoned). This 'Jactou' variety is marketed under the MIDAS TOUCH trademark. The 'Meirouve' variety is marketed under the ALPHONSE DAUDET trademark. The 'Meizoele' variety is marketed under the GLOWING PEACE and PHILIPPE NOIRET trademarks. The parentage of the new variety can be summarized as follows:

('Just Joey'×'Jactou')×('Meirouve'×'Meizoele')

The seeds resulting from the above pollination were sown and small plants were obtained which were physically and biologically different from each other. Selective study resulted in the identification of a single plant of the new variety.

It was found that the new Hybrid Tea rose plant of the present invention:

(a) forms vigorous upright vegetation, (b) forms pointed ovoid-shaped buds, (c) forms attractive fragrant double blossoms having a soft apricot-pink coloration, (d) displays attractive glossy medium green foliage, (e) displays above average disease resistance for the class, and (f) is particularly well suited for providing attractive ornamentation in the landscape.

The new variety well meets the needs of the horticultural industry and can be grown to advantage in parks and gardens.

The new variety can be readily distinguished from its ancestors. For instance, the blossom coloration is considerably different from that of the 'Just Joey', 'Jactou', 'Meirouve' and 'Meizoele' varieties. More specifically, the 'Just Joey' forms buff-orange blossoms, the 'Jactou' variety forms yellow blossoms, the 'Meirouve' variety forms apricot blossoms, and 'Meizoele' variety forms golden amber blossoms.

The new variety has been found to undergo asexual propagation at Wasco, Calif., U.S.A., by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meibidull', and will be marketed under the APRICOT CANDY trademark.

BRIEF DESCRIPTION OF THE PHOTOGRAPH

The accompanying photograph shows as nearly true as it is reasonably possible to make the same, in a color illustration of this character, a typical specimen of the new variety. A partially open blossom, a near fully open blossom, and floral buds in various stages of development are illustrated. The illustrated plant was approximately two years of age, had been asexually reproduced by budding, and was being grown outdoors at Wasco, Calif., U.S.A.

DETAILED DESCRIPTION

The chart used in the identification of the colors is that of The Royal Horticultural Society (R.H.S. Colour Chart) except where ordinary color terms are utilized. Such common color terms are to be accorded their customary dictionary significance. The description is based upon the observation of plants of the new variety at an age of approximately two years during the month of July while being grown near West Grove, Pa., U.S.A.

Class: Hybrid Tea.

Plant:

*Growth habit.*—Vigorous upright.

*Blooming habit.*—Recurrent.

*Height.*—Commonly approximately 5 feet at an age of two years.

*Width.*—Commonly approximately 2-½ feet at an age of two years.

Branches:

*Color.*—Young stems: commonly near Yellow-Green Group 146D. adult wood: commonly near Yellow-Green Group 147C.

*Thorns.*—Size: larger thorns commonly are approximately 5 mm in length and possess a base which measures approximately 5 mm. quantity: commonly approximately 21 on average on main stocks, and approximately 53 on average on laterals. color: commonly near Yellow-Green Group 145C at the tip and near Greyed-Orange Group 176C at the base both when young and when mature.

Leaves:

*Petioles.*—Commonly near Greyed-Green Group 194A in coloration.

*Rachis.*—Commonly near Greyed-Orange Group 176A in coloration. texture: smooth.

*Leaflets.*—Shape: generally ovate. number: commonly 5 or 7 per leaf. size: the terminal leaflets commonly are approximately 5 cm in length on average, and approximately 3 cm in width on average. serration: small and single. texture: smooth and glossy on the upper surface. color (young foliage): near Yellow-Green Group 146A. color (adult foliage): near Yellow-Green Group 147A.

Inflorescence:

*Number of flowers.*—Commonly approximately 1 blossom per stem.

*Peduncle.*—Moderately strong, commonly approximately 5 cm in length on average, pubescent, and near Yellow-Green Group 144A in coloration.

*Sepals.*—Texture: somewhat rough. color: Green Group 143C.

*Buds.*—Shape: ovoid, pointed, and commonly with a leafy tip. length: approximately 3 cm on average. width: approximately 1.5 cm at the widest point on average. color as calyx breaks: commonly near Yellow-Green Group 146C.

*Flower.*—Shape: high-centered. diameter: approximately 8 cm on average. color (newly opened): upper surface: near Red Group 38A. under surface: near Red Group 37C. color (open for three days): upper side: commonly between Red Group 37B and Red Group 38B with Yellow Group 7B at the point of attachment. under side: commonly between Red Group 38C and Red Group 39C with Yellow Group 7B at the point of attachment. color stability: with full maturity some brownish discoloration may appear on the under sides of the petals nearest the sepals. fragrance: pleasant and somewhat spicy. lasting quality: the blossoms commonly last approximately 5 days on average on the plant, and approximately 4 to 5 days on average when cut and placed in a vase. petal number: approximately 25 on average under normal growing conditions. petal shape: classic for a Hybrid tea rose. petal texture: smooth. petal arrangement: imbricated. petal drop: good with the petals commonly detaching cleanly before drying. stamen number: approximately 80 to 90 on average. anthers: regularly arranged around the styles, commonly approximately 2 to 3 mm in size on average, and near Greyed-Orange Group 166A in coloration. pollen: present, and near Greyed-Orange Group 167C in coloration. filaments: commonly approximately 1 cm in length on average, and near Yellow Group 9B in coloration. pistils: approximately 60 to 70 on average. styles: commonly near Greyed-Yellow Group 162B in coloration. hips: none available for inspection.

Development:

*Vegetation.*—Vigorous.

*Blooming.*—Recurrent.

*Tolerance to diseases.*—Above average for the class; however, not completely resistant to Black Spot and Mildew during observations to date.

I claim:

1. A new and distinct Hybrid Tea rose plant characterized by the following characteristics:

(a) forms vigorous upright vegetation, (b) forms pointed ovoid-shaped buds, (c) forms attractive fragrant double blossoms having a soft apricot-pink coloration, (d) displays attractive glossy medium green foliage, (e) displays above average disease resistance for the class, and, (f) is particularly well suited for providing attractive ornamentation in the landscape;

substantially as shown and described.

* * * * *